United States Patent
Shim

(10) Patent No.: US 10,561,684 B2
(45) Date of Patent: Feb. 18, 2020

(54) PHARMACEUTICAL COMPOSITION FOR PREVENTING OR TREATING SENSORINEURAL HEARING LOSS OR TINNITUS INCLUDING PLATELET-RICH PLASMA AND METHOD USING THE SAME

(71) Applicant: Min Bo Shim, Gyeonggi-do (KR)

(72) Inventor: Min Bo Shim, Gyeonggi-do (KR)

(73) Assignee: Min Bo Shim, Gyeonggi-do (KR)

(*) Notice: Subject to any disclaimer, the term of this patent is extended or adjusted under 35 U.S.C. 154(b) by 567 days.

(21) Appl. No.: 15/166,415

(22) Filed: May 27, 2016

(65) Prior Publication Data
US 2017/0056447 A1 Mar. 2, 2017

(30) Foreign Application Priority Data

Aug. 27, 2015 (KR) .................. 10-2015-0121038
May 11, 2016 (KR) .................. 10-2016-0057806

(51) Int. Cl.

| | | |
|---|---|---|
| A61K 36/00 | (2006.01) | |
| A61K 35/16 | (2015.01) | |
| A61K 35/19 | (2015.01) | |
| A61K 31/573 | (2006.01) | |
| A61K 9/00 | (2006.01) | |
| A61K 31/525 | (2006.01) | |
| A61K 31/4415 | (2006.01) | |
| A61K 31/164 | (2006.01) | |
| A61K 31/51 | (2006.01) | |
| A61K 31/714 | (2006.01) | |
| A61K 31/455 | (2006.01) | |
| A61K 31/4188 | (2006.01) | |

(52) U.S. Cl.
CPC ............ *A61K 35/16* (2013.01); *A61K 9/0046* (2013.01); *A61K 31/164* (2013.01); *A61K 31/4188* (2013.01); *A61K 31/4415* (2013.01); *A61K 31/455* (2013.01); *A61K 31/51* (2013.01); *A61K 31/525* (2013.01); *A61K 31/573* (2013.01); *A61K 31/714* (2013.01); *A61K 35/19* (2013.01)

(58) Field of Classification Search
CPC ..................................... A61K 36/00
USPC ........................................ 424/725
See application file for complete search history.

(56) References Cited

U.S. PATENT DOCUMENTS

2014/0073835 A1* 3/2014 Shapiro ................ A61M 37/00
600/9

FOREIGN PATENT DOCUMENTS

| KR | 2013-0012552 | 2/2013 |
| KR | 2015-0061806 | 6/2015 |
| RU | 2319508 | 3/2008 |
| RU | 2008109703 A | 9/2009 |
| WO | WO 2012/092458 | 7/2012 |
| WO | WO 2014/179834 | 11/2014 |

OTHER PUBLICATIONS

Erkilet et al., The Journal of Laryngology and Otology, 2009, 123, 482-487.*
Yu Qing et al., "Research progress in post-traumatic platelet-rich plasma therapy", International Journal of Orthopaedics, Jul. 31, 2008, vol. 29, No. 4, pp. 272-274, English abtract 1 page.
Duan Maoli et al., "Prevention and treatment of sensorineural deafness", Chinese Journal of Otology, Dec. 31, 2006, vol. 4, No. 1, pp. 34-38, English abstract 1 page.
Du Gang et al., "Effects of platelet-rich plasma combined with bone marrow mesenchymal stem cells on NGF and BDNF after spinal cord injury in rats", Chinese Journal of Osteoporosis, Jan. 31, 2014, vol. 20, No. 1, pp. 29-32.
Semenov F.V. et al. The effect of topical use of platelet-rich plasma on the condition of inner ear on a stapedoplasty// Rossiiskaya otorinolaringologiya, N 4 (35), 2008, pp. 161-164.
Semenov F.V. et al. (The use of platelet-rich plasma for preventing cochleovestibular disorders on a stapedoplasty// Vestnik otorinolaringologii, N 3, 2011 [Online][ Internet site: http://www.mediasphera.ru/uppic/Vestn%20otorinolaringol/2011/3/12/LOR_2011_03_47.pdf
"The Secret Behind PRP Injection's Immortality," May 29, 2015, retrieved from http://drprpusa.com/the-secret-behind-prp-injections-immortality/, on Nov. 7, 2016, 6 pages.
Baek, "Sensorineural Hearing Loss: Causes and Hearing Rehabilitation," Hanyang Med Rev, 35:57-65, 2015, with English abstract.
Erkilet et al., "Platelet-rich plasma improves healing of tympanic membrane perforations: experimental study," The Journal of Laryngology & Otology, 123, 482-487, 2009.

* cited by examiner

*Primary Examiner* — Michael V Meller
(74) *Attorney, Agent, or Firm* — Kenneth H. Sonnenfeld; Kristine Waddell

(57) ABSTRACT

Provided are a pharmaceutical composition for preventing or treating sensorineural hearing loss or tinnitus including platelet-rich plasma, and a method of preventing or treating sensorineural hearing loss or tinnitus using the same.

9 Claims, 1 Drawing Sheet

PHARMACEUTICAL COMPOSITION FOR PREVENTING OR TREATING SENSORINEURAL HEARING LOSS OR TINNITUS INCLUDING PLATELET-RICH PLASMA AND METHOD USING THE SAME

CROSS-REFERENCE TO RELATED APPLICATION

This application claims the benefit of Korean Patent Application No. 10-2015-0121038, filed on Aug. 27, 2015, and Korean Patent Application No. 10-2016-0057806, filed on May 11, 2016, in the Korean Intellectual Property Office, the disclosures of which are incorporated herein in their entirety by reference.

BACKGROUND

1. Field

The present disclosure relates to a pharmaceutical composition for preventing or treating sensorineural hearing loss or tinnitus including platelet-rich plasma, and a method of preventing or treating sensorineural hearing loss or tinnitus using the same.

2. Description of the Related Art

An ear is compartmentalized into outer ear, middle ear, and inner ear. The outer ear includes the auricle and the external auditory canal. The middle ear consists of the eardrum, the tympanic cavity, the auditory ossicles, and the eustachian tube, and the inner ear consists of the vestibular organ, three semicircular canals, and the cochlear canal. Since sound is acoustic energy, sound is transmitted from the auricle through the external auditory canal to vibrate the eardrum. The vibration of the eardrum is transmitted to the auditory ossicle composed of 3 small bones connected to the eardrum via mechanical energy. Strapes, the distal bone of the auditory ossicle, is connected to the cochlear canal, thereby transmitting the energy to the lymph in the cochlear canal. Transmitted energy induces waves in the lymph by which hair cells inside the cochlear canal are stimulated. The movement of hair cells causes ionic change, and therefore, neurotransmitters are transferred to the auditory nerve attached to hair cells, in which acoustic sound is transmitted to the brain as electric energy.

Hearing loss may be generally divided into conductive hearing loss and sensorineural hearing loss. Conductive hearing loss is caused by impairment in sound transmitting organs such as the outer ear, the eardrum, the middle ear, etc., and sensorineural hearing loss is caused by a disorder in a sound sensing function of the cochlear canal, or a dysfunction in the auditory nerve or central nerve system which transmits auditory stimuli to the brain. Surgical treatment of conductive hearing loss is possible. Sensorineural hearing loss is aided by an assistant means such as hearing aids or artificial ear cochlear implant. However, if the degree of hearing loss is severe, the effectiveness is low with a huge difference from normal hearing ability, and thus lots of inconvenience in daily life remains. Meanwhile, tinnitus refers to an auditory perception without an external auditory stimulus, and there is no therapy available for the treatment of tinnitus.

Accordingly, there is a need for a composition effective for prevention or treatment of sensorineural hearing loss or tinnitus and a method of preventing or treating sensorineural hearing loss or tinnitus using the same.

SUMMARY

An aspect provides a pharmaceutical composition for preventing or treating sensorineural hearing loss or tinnitus.

Another aspect provides a method of preventing or treating sensorineural hearing loss or tinnitus.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
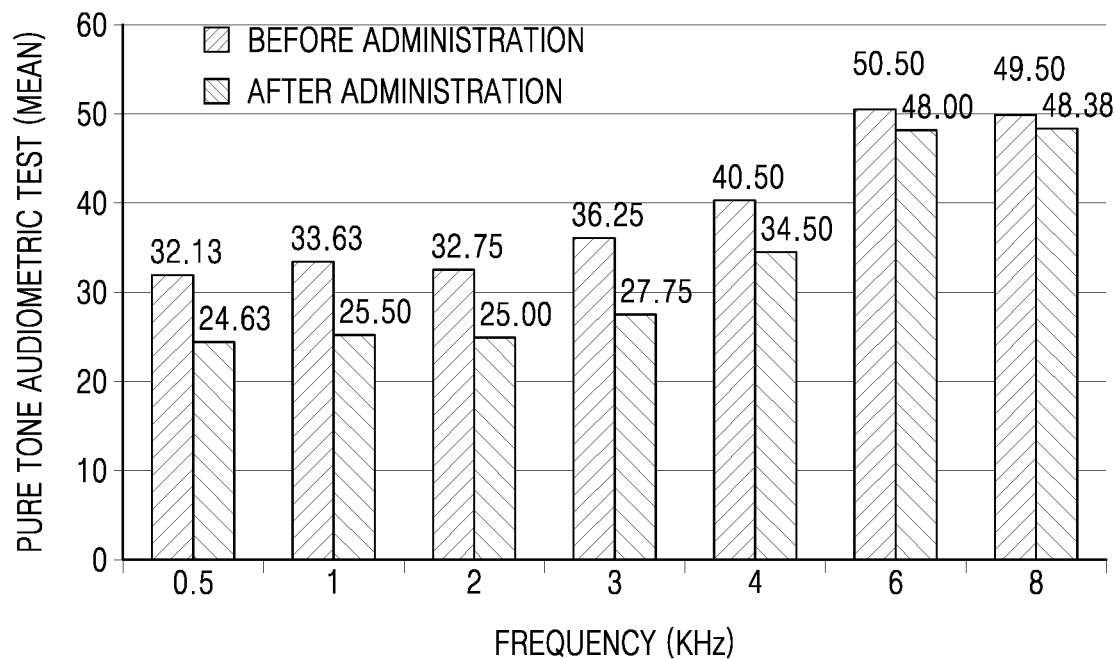
FIG. 1 is a graph showing results of a pure-tone audiometric test of left ear at each frequency (KHz)

An aspect provides a pharmaceutical composition for preventing or treating sensorineural hearing loss or tinnitus, the pharmaceutical composition including platelet-rich plasma.

The term "platelet-rich plasma (PRP)" refers to plasma containing concentrated platelet, compared to blood obtained from a subject. The PRP may be PRP immediately after being isolated from blood of a subject, PRP incubated at room temperature for about 1 minute to about 40 minutes after being isolated from blood of the subject, or a combination thereof. The PRP may be incubated at room temperature for about 1 minute to about 40 minutes, about 3 minutes to about 35 minutes, about 5 minutes to about 30 minutes, about 8 minutes to about 25 minutes, about 10 minutes to about 25 minutes, or about 15 minutes to about 25 minutes after being isolated from blood of the subject. The PRP immediately after being isolated from blood of the subject and the PRP incubated at room temperature for about 1 minute to about 40 minutes after being isolated from blood of the subject may be separate compositions. The PRP incubated at room temperature for about 1 minute to about 40 minutes may have a viscosity about 1.1 times or higher, about 1.5 times or higher, about 2 times or higher, or about 5 times or higher than that of the PRP immediately after being isolated from blood of the subject. For example, the PRP immediately after being isolated from blood of the subject may have a viscosity of about 1 miliPascal-second (mPa·s or centi Poise (cP)) to about 5 mPa·s, about 2 mPa·s to about 4 mPa·s, or about 2 mPa·s to about 3 mPa·s. The PRP incubated at room temperature for about 1 minute to about 40 minutes may have a viscosity of about 5 mPa·s to about 20 mPa·s, about 8 mPa·s to about 18 mPa·s, about 10 mPa·s to about 15 mPa·s, or about 12 mPa·s to about 14 mPa·s. Since the PRP immediately after being isolated from blood of the subject has a low viscosity, the PRP may be rapidly discharged through the eustachian tube when administered to the tympanic cavity. Since the PRP incubated at room temperature for about 1 minute to about 40 minutes after being isolated from blood of the subject has a high viscosity, the PRP may be slowly discharged through the eustachian tube when administered to the tympanic cavity. Since PRP having a high viscosity is slowly discharged from the ear, the PRP may contact nerve cells in the inner ear for a long time. The nerve cells in the inner ear may be regenerated by the PRP.

The PRP may be for autologous blood administration. For example, PRP is prepared from blood collected from a subject, and then the prepared PRP may be administered to the subject again.

The pharmaceutical composition may further include a second pharmaceutical composition which is known to be effective for sensorineural hearing loss or tinnitus. The second pharmaceutical composition and the above pharmaceutical composition may be administered at the same time or separately. The second pharmaceutical composition may be a composition for administration to the tympanic cavity or for intravenous administration. The second pharmaceutical composition may be dexamethasone, vitamin B1, vitamin B6, vitamin B12, thiamine hydrochloride, pyridoxine hydrochloride, nicotinamide, D-panthenol, cyanocobalamin, riboflavin, biotin, Pan-B-Comp injection, or a combination thereof.

The pharmaceutical composition may further include a blood clotting accelerant. The blood clotting accelerant may be a factor related to blood clotting. The blood clotting accelerant may coagulate PRP. For example, the blood clotting accelerant may be thrombin, calcium chloride, calcium gluconate, or a combination thereof. The blood clotting accelerant and the above pharmaceutical composition may be administered at the same time or separately. The blood clotting accelerant may be for administration to the tympanic cavity.

The pharmaceutical composition may be for administration to the tympanic cavity. The tympanic cavity refers to a part of the middle ear, which is a space between the outer ear and the inner ear. The pharmaceutical composition may be administered to the tympanic cavity through the eardrum.

The term "hearing loss", as known as hearing impairment, is a partial or total inability to hear.

The term "sensorineural hearing loss" refers to hearing loss caused by a disorder in a sound sensing function of the cochlear canal, or a dysfunction in the auditory nerve or central nerve system which transmits auditory stimuli to the brain.

The sensorineural hearing loss may be presbycusis; noise-induced hearing loss; sudden hearing loss; Meniere's disease; autoimmune hearing loss; ischaemic hearing loss; head injury-associated hearing loss; ototoxic drug-associated hearing loss; genetic hearing loss; damage to the organ of corti, caused by viral or bacterial infection, or functional disorder of the organ of corti, caused by other causes or by unknown causes; or a combination thereof. The sensorineural hearing loss may be caused by inflammatory diseases such as labyrinthitis, encephalomeningitis, etc.; noise-induced hearing loss; ototoxic drug; trauma such as temporal bone fracture, etc.; presbycusis; Meniere's disease; sudden sensorineural hearing loss; metabolic disorders such as hypothyroidism, etc.; ischemic cerebrovascular disease; blood diseases such as leukemia, etc.; neurological disorders such as multiple sclerosis, etc.; immune disorders; neoplastic diseases such as acoustic neuroma, etc; bone diseases; and genetic diseases such as Waardenburg syndrome, Usher syndrome, etc. Presbycusis is age-related hearing loss and it is a part of the normal aging process. Presbycusis may be caused by degeneration of the receptor cells in the spiral organ of corti in the inner ear. Noise-induced hearing loss may be caused by a long-duration exposure to noise, for example, loud music, heavy equipment or mechanical device, airplanes, bombardment, or noise caused by other persons.

The term "tinnitus" refers to an auditory perception without an external auditory stimulus. Tinnitus may occur in one ear or both ears either constantly or sporadically, and is commonly described as a ringing.

The term "prevention" means all of the actions by which the occurrence of sensorineural hearing loss or tinnitus is restrained or retarded by administration of the composition, and the term "treatment" means all of the actions by which the symptoms of sensorineural hearing loss or tinnitus have taken a turn for the better or been modified favorably by administration of the composition.

The pharmaceutical composition may include the PRP in an effective amount. The effective amount may be properly selected depending on a subject, and determined depending on the severity of disease, a patient's age, body weight, health conditions, gender, and drug sensitivity, administration time, administration route, excretion rate, treatment period, and drugs blended with or co-administered with the composition of the present invention, and other factors well known in the medical field. The effective amount may be about 0.01 ml to about 1 ml, about 0.1 ml to about 1 ml, or about 0.5 ml to about 1 ml per ml of the pharmaceutical composition.

The pharmaceutical composition may further include a carrier, an excipient, or a diluent. The carrier, excipient, and diluent may include, for example, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oils or a combination thereof.

The pharmaceutical composition may be an injectable formulation.

The administration dose of the pharmaceutical composition may be, for example, about 0.01 ml to about 5 ml, about 0.1 ml to about 4 ml, about 0.5 ml to about 3 ml, about 0.5 ml to about 2 ml, or about 1 ml per adult. The pharmaceutical composition may be administered, for example, once a day, twice or ten times a day, or every other day to once a year. The pharmaceutical composition may be administered, for example, twice, three times, four times, five times, six times, eight times, ten times, twelve times, or fifteen times or more every two days, every three days, every four days, every five days, every thirty days, every 2 months, every 4 months, or every 6 months.

Another aspect provides a method of preventing or treating sensorineural hearing loss or tinnitus, the method including administering platelet-rich plasma to the tympanic cavity of a subject.

The platelet-rich plasma, tympanic cavity, sensorineural hearing loss, tinnitus, prevention, and treatment are the same as described above.

The subject may be a subject having sensorineural hearing loss or tinnitus or at the risk of having sensorineural hearing loss or tinnitus. The subject may be a mammal, for example, a human, a cow, a horse, a pig, a dog, a sheep, a goat, or a cat.

The method may further include administering a second pharmaceutical composition, which is known to be effective for sensorineural hearing loss or tinnitus. The method may further include administering dexamethasone, vitamin B1, vitamin B6, vitamin B12, thiamine hydrochloride, pyridoxine hydrochloride, nicotinamide, D-panthenol, cyanocobalamin, riboflavin, biotin, Pan-B-Comp injection, or a combination thereof. The second pharmaceutical composition and the PRP may be administered to the tympanic cavity of the subject or intravenously at the same time or sequentially.

The method may further include administering the blood clotting accelerant. The method may further include administering thrombin, calcium chloride, calcium gluconate, or a combination thereof. The blood clotting accelerant and the PRP may be administered to the tympanic cavity at the same time or sequentially.

The method may include obtaining PRP from the blood of a subject; and administering the obtained PRP to the tympanic cavity of the subject. The blood of the subject may be blood containing no anticoagulant. The anticoagulant may be, for example, ethylenediaminetetraacetate (EDTA), oxalate, citrate, and heparin. When the blood of the subject may be blood containing the anticoagulant, the blood clotting accelerant may be administered together with PRP. The obtaining of the PRP from the blood of the subject may be performed by, for example, centrifugation. The centrifugation may be performed at about 4° C. to about 37° C., at about 10° C. to about 37° C., or at room temperature. The centrifugation may be performed at a speed of about 3,500 rpm to about 5,000 rpm, about 4,000 rpm to about 4,500 rpm, or about 4,200 rpm. The centrifugation may be performed for about 1 minute to about 20 minutes, about 1 minute to about 10 minutes, about 1 minute to about 5 minutes, or about 5 minutes. Since the PRP obtained from the subject is administered to the subject again, the administration may be autologous blood administration. The administering may include administering to the tympanic cavity PRP immediately after being isolated from the blood of the subject, and administering to the tympanic cavity PRP incubated at room temperature for about 1 minute to about 40 minutes after being isolated from the blood of the subject. Since the PRP immediately after being isolated from blood of the subject has a low viscosity, the PRP may be rapidly discharged through the eustachian tube when administered to the tympanic cavity. Since the PRP incubated at room temperature for about 1 minute to about 40 minutes after being isolated from blood of the subject has a high viscosity, the PRP may be slowly discharged through the eustachian tube when administered to the tympanic cavity. Since PRP having a high viscosity is slowly discharged from the ear, the PRP may contact nerve cells in the inner ear for a long time. The nerve cells in the inner ear may be regenerated by the PRP.

The PRP may be administered, for example, in an amount of about 0.01 ml to about 5 ml, about 0.1 ml to about 4 ml, about 0.5 ml to about 3 ml, about 0.5 ml to about 2 ml, or about 1 ml per adult. The PRP may be administered, for example, once a day, twice or ten times a day, or every other day to once a year. The PRP may be administered, for example, twice, three times, four times, five times, six times, eight times, ten times, twelve times, or fifteen times or more every two days, every three days, every four days, every five days, every thirty days, every 2 months, every 4 months, or every 6 months.

According to the pharmaceutical composition for preventing or treating sensorineural hearing loss or tinnitus including platelet-rich plasma of an aspect, and the method using the same, sensorineural hearing loss or tinnitus of a subject may be prevented or treated in an easy and efficient manner.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in more detail with reference to Examples. However, these Examples are for illustrative purposes only, and the scope of the invention is not intended to be limited by these Examples.

Example 1

Verification of Prophylactic or Therapeutic Effect of Platelet-Rich Plasma on Hearing Loss or Tinnitus In order to examine whether platelet-rich plasma exhibits a prophylactic or therapeutic effect on hearing loss or tinnitus, its clinical efficacy was evaluated.

1. Selection of Subject and Performance of Pure-Tone Audiometric Test

An audiometric test of a subject was performed by a pure-tone audiometric test. An endoscope was introduced into the outer ear canal of the subject to observe the eardrum of the subject. The subjects having sensorineural hearing loss without impairment in the outer ear and the middle ear were subjected to the pure-tone audiometric test.

The pure-tone audiometric test is a method of measuring a pure tone hearing threshold at each tone frequency, and hearing thresholds were measured at frequencies of 0.5 KHz, 1 KHz, 2 KHz, 3 kHz, 4 kHz, 6, kHz, and 8 kHz.

In the pure-tone audiometric test, an average intensity of a tone audible to a healthy young normal person was determined as 0 decibel (dB), and based on this, the intensity of the tone was increased in 5 dB steps. The intensity of the tone which could be first heard by the subject at each frequency, that is, threshold was measured. As a test level at each frequency was lower, the ear could be more sensitive, indicating good hearing. For example, it may be determined that if the test level is 40 dB or lower, there are no problems in daily life, and if the test level is 5 dB to 10 dB, the subject is a normal person having no hearing problem.

2. Hearing-Improving Effects of Platelet-Rich Plasma and Dexamethasone

PRP was administered to the tympanic cavity of each of the subjects having sensorineural hearing loss who were selected in 1, and then hearing recovery was examined.

First, to examine hearing of the subjects (n=20) before PRP administration, a pure-tone audiometric test was performed on the right ear ("RT") and the left ear ("LT") of each subject using a pure-tone audiometric tester, Earscan (Micro Audiometrics). Results of the pure-tone audiometric test were obtained from the subjects before administration of PRP to their tympanic cavity. Of the subjects, one subject was administered with dexamethasone nineteen times, but no hearing improvement was observed.

Thereafter, the eardrum of each subject was locally anesthetized with Emla Cream 5% (AstraZeneca, Korea).

About 10 ml to about 20 ml of blood was collected from the vein of the subject. During the blood collection, a blood collection tube containing no anticoagulant was used. The collected blood was centrifuged at room temperature for about 5 minutes at a speed of about 4,200 rpm. About 3 ml to about 4 ml of a middle layer having a high level of platelets was obtained from the centrifuged blood to prepare PRP. Viscosity of the prepared PRP was about 2 mPa·s to about 3 mPa·s (micro VISC, RHEOSENSE, INC.).

Immediately after obtaining the PRP, about 3 ml to about 4 ml of the obtained PRP was divided into 3 or 4 of 1 ml-syringes, and then each 1 ml was injected into the tympanic cavities of both ears of the subject at 30-minute intervals.

PRP was incubated at room temperature for about 15 minutes to about 25 minutes after obtaining PRP. Viscosity of the incubated PRP was about 12 mPa·s to about 14 mPa·s. Each about 0.5 ml to about 1 ml of the incubated PRP was injected into the tympanic cavities of both ears of the subject.

In this method, PRP was administered twice a week for six times in total. Of the total six times, the first three times were for PRP administration, and the other three times were for administration of dexamethasone (Jeil Pharmaceutical Co., Ltd.), in which 1 ml of dexamethasone was injected into the tympanic cavities of both ears of the subject, and then PRP was injected thereto.

About 2 days to about 120 days after initial administration of PRP, the pure-tone audiometric test was performed as described in 1. From the obtained test results, to examine a difference between before administration and after administration at each frequency, an SPSS WIN 18.0 program was used to perform the t-test.

Figure 2:
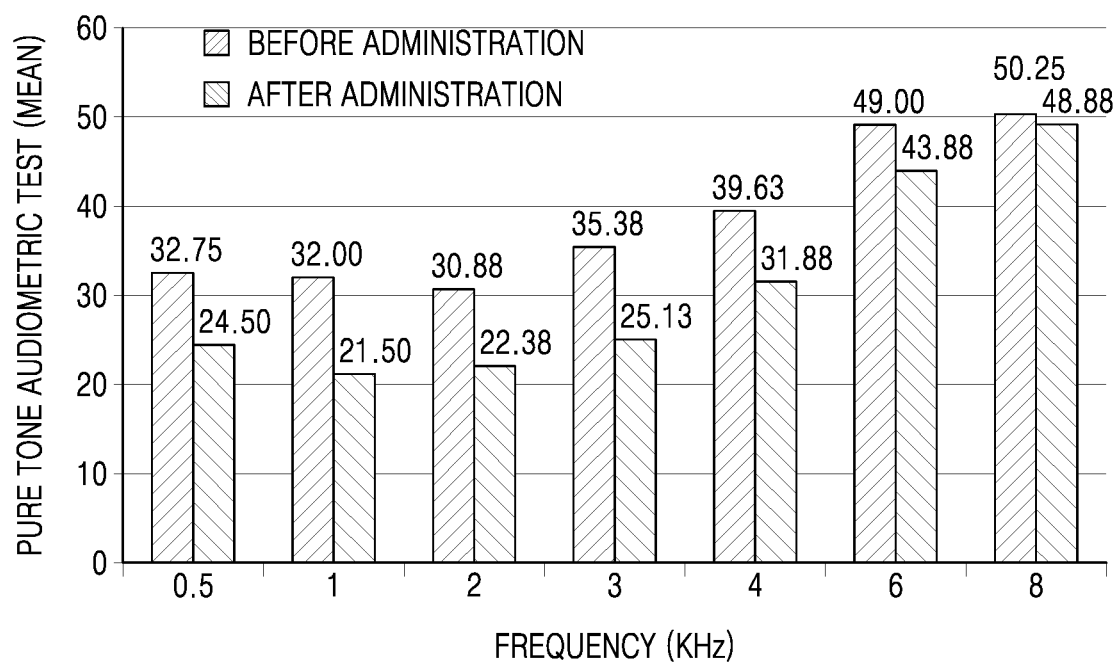
FIG. 2 is a graph showing results of a pure-tone audiometric test of right ear at each frequency (KHz).

Pure-tone audiometric test results of the left and right ears are given in Tables 1 and 2, respectively and graphs thereof are shown in FIGS. 1 and 2, respectively.

TABLE 1

Pure tone hearing of left ear before administration and after administration at each frequency (n = 40)

| Frequency (KHz) | Before administration | | After administration | | t | p |
|---|---|---|---|---|---|---|
| | Mean | Standard deviation | Mean | Standard deviation | | |
| 0.5 | 32.13 | 26.1869 | 24.63 | 22.7130 | 2.837 | 0.007** |
| 1 | 33.63 | 26.6503 | 25.50 | 22.8933 | 3.786 | 0.001** |
| 2 | 32.75 | 25.2411 | 25.00 | 22.2745 | 4.466 | 0.000*** |
| 3 | 36.25 | 25.6393 | 27.75 | 22.6724 | 5.627 | 0.000*** |
| 4 | 40.50 | 25.4649 | 34.50 | 23.8800 | 3.237 | 0.002** |
| 6 | 50.50 | 25.5403 | 48.00 | 25.4397 | 0.995 | 0.326 |
| 8 | 49.50 | 26.0128 | 48.38 | 29.2730 | 0.425 | 0.673 |

(*p < 0.05; p < 0.01; and *p < 0.001)

TABLE 2

Pure tone hearing of right ear before administration and after administration at each frequency (n = 40)

| KHz | Before administration | | After administration | | t | p |
|---|---|---|---|---|---|---|
| | Mean | Standard deviation | Mean | Standard deviation | | |
| 0.5 | 32.75 | 27.3146 | 24.50 | 23.1439 | 2.359 | 0.023* |
| 1 | 32.00 | 26.2337 | 21.50 | 18.3694 | 4.170 | 0.000*** |
| 2 | 30.88 | 27.5003 | 22.38 | 20.6307 | 3.913 | 0.000*** |
| 3 | 35.38 | 28.4512 | 25.13 | 22.0863 | 4.418 | 0.000*** |
| 4 | 39.63 | 28.5861 | 31.88 | 25.0304 | 3.069 | 0.004** |
| 6 | 49.00 | 27.1322 | 43.88 | 24.8969 | 2.311 | 0.026* |
| 8 | 50.25 | 28.6658 | 48.88 | 30.5397 | 0.510 | 0.613 |

(*p < 0.05; p < 0.01; and *p < 0.001)

As shown in Table 1 and FIG. 1, test levels of the left ears were significantly decreased at frequencies of about 0.5 KHz to about 4 KHz. Further, as shown in Table 2 and FIG. 2, test levels of the right ears were significantly decreased at frequencies of about 0.5 KHz to about 6 KHz. The subjects' hearing was significantly improved by administration of PRP and/or dexamethasone to the tympanic cavity. Therefore, it was confirmed that dexamethasone and PRP exhibit prophylactic or therapeutic effects on sensorineural hearing loss or tinnitus.

3. Hearing-Improving Effects of High-Viscosity Platelet-Rich Plasma

In order to examine whether high-viscosity sticky PRP exhibits a hearing-improving effect, a subject having sensorineural hearing loss without impairment in the outer ear and the middle ear was selected.

As described in 2, PRP was obtained from the blood of the selected subject, and the obtained PRP was incubated at room temperature for about 15 to 25 minutes to obtain PRP having a viscosity of about 12 mPa to about 14 mPa. 0.5 ml of the obtained PRP was injected into the tympanic cavities of the both ears of the subject using a syringe. Unlike in 2, dexamethasone and PRP immediately after being obtained were not administered.

Pure-tone audiometric test results before administration and after administration of high-viscosity PRP to the tympanic cavities of the subject are given in Table 3 ("NRM": not readily measurable by pure-tone audiometry).

TABLE 3

| No. of subject | | Before PRP administration (dB) Frequency (KHz) | | | | | | | After PRP administration (dB) Frequency (KHz) | | | | | | |
|---|---|---|---|---|---|---|---|---|---|---|---|---|---|---|---|
| | | 0.5 | 1 | 2 | 3 | 4 | 6 | 8 | 0.5 | 1 | 2 | 3 | 4 | 6 | 8 |
| 33 | RT | 65 | 85 | 80 | 65 | 80 | 85 | 70 | 65 | 70 | 75 | 60 | 65 | 80 | NRM |
| | LT | 35 | 30 | 25 | 65 | 80 | 80 | 70 | 35 | 25 | 25 | 65 | 70 | 75 | 60 |

In Table 3, when the levels at each frequency were compared between before and after administrations of high-viscosity PRP to the tympanic cavity, compared to those before administration, it was found that the levels after administration of high-viscosity PRP to the tympanic cavity decreased. The subject's hearing was improved only by administration of high-viscosity PRP. Therefore, it was confirmed that PRP exhibits a prophylactic or therapeutic effect on sensorineural hearing loss or tinnitus.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of treating sensorineural hearing loss or tinnitus in a human or animal in need thereof, comprising administering a therapeutically effective amount of platelet-rich plasma to the tympanic cavity of the human or animal in need thereof wherein the human or animal has no injury to the eardrum.

2. The method of claim 1, wherein the platelet-rich plasma is autologous platelet-rich plasma.

3. The method of claim 1, further comprising administering one or more therapeutic agents selected from the group consisting of dexamethasone, vitamin B1, vitamin B6, vitamin B12, thiamine hydrochloride, pyridoxine hydrochloride, nicotinamide, D-panthenol, cyanocobalamin, riboflavin, biotin, and Pan-B-Comp injection.

4. The method of claim 1, further comprising administering a blood clotting accelerant.

5. The method of claim 1, comprising obtaining platelet-rich plasma from the blood of a human or animal in need thereof; and administering the obtained platelet-rich plasma to the tympanic cavity of the human or animal in need thereof.

6. The method of claim 1, wherein the administering comprises administering platelet-rich plasma to the tympanic cavity of the human or animal in need thereof immediately after being isolated from the blood of the human or animal and incubated at room temperature for about 1 minute to about 40 minutes after being isolated from the blood of the human or animal in need thereof.

7. The method of claim 1, wherein the human or animal has tinnitus.

8. The method of claim 1, wherein the human or animal has sensorineural hearing loss.

9. The method of claim 1, wherein the human or animal is human.

* * * * *